(12) United States Patent
Entenman et al.

(10) Patent No.: US 7,316,666 B1
(45) Date of Patent: Jan. 8, 2008

(54) FLUID WARMING CASSETTE WITH RAILS AND A STIFFENING MEMBER

(75) Inventors: Scott A. Entenman, St. Paul, MN (US); Wayne E. Schmidt, Lakeville, MN (US)

(73) Assignee: Arizant Healthcare Inc., Eden Prairie, MN (US)

( * ) Notice: Subject to any disclaimer, the term of this patent is extended or adjusted under 35 U.S.C. 154(b) by 254 days.

(21) Appl. No.: 10/822,580

(22) Filed: Apr. 12, 2004

(51) Int. Cl.
*A61F 7/12* (2006.01)

(52) U.S. Cl. .................. 604/113; 604/114; 392/465; 392/470

(58) Field of Classification Search ............... 604/113, 604/114, 6.13, 403, 408; 392/465, 470, 479; 222/146.1, 146.2, 146.5; 165/46; 607/112; 219/518
See application file for complete search history.

(56) References Cited

U.S. PATENT DOCUMENTS

| | | | |
|---|---|---|---|
| 2,979,310 A | 4/1961 | Nicholson | 257/247 |
| 2,992,545 A | 7/1961 | Walker | 62/515 |
| 3,140,716 A | 7/1964 | Harrison et al. | 128/339 |
| 3,424,238 A | 1/1969 | Leeds et al. | 165/133 |
| 3,485,245 A | 12/1969 | Lahr et al. | 128/272 |
| 3,640,283 A | 2/1972 | Bhatia | 128/399 |
| 4,131,200 A | 12/1978 | Rinfret | 206/484 |
| 4,227,525 A * | 10/1980 | Lundquist | 604/126 |
| 4,476,685 A | 10/1984 | Aid | 62/3 |
| 4,568,330 A * | 2/1986 | Kujawski et al. | 604/83 |
| 4,574,876 A | 3/1986 | Aid | 165/46 |
| 4,602,910 A | 7/1986 | Larkin | 604/87 |
| 4,707,587 A * | 11/1987 | Greenblatt | 392/466 |
| 4,709,534 A | 12/1987 | Sengewald | 53/452 |
| 4,731,072 A | 3/1988 | Aid | 604/408 |
| 4,734,269 A | 3/1988 | Clarke et al. | 422/310 |
| 4,744,414 A | 5/1988 | Schon | 165/167 |
| 4,847,470 A | 7/1989 | Bakke | 219/299 |
| 4,887,913 A | 12/1989 | Sengewald | 383/96 |
| 4,919,134 A | 4/1990 | Streeter | 128/400 |
| 4,919,326 A | 4/1990 | Deiger | 229/109 |

(Continued)

FOREIGN PATENT DOCUMENTS

EP      0 095 526      10/1982

(Continued)

OTHER PUBLICATIONS

Whittington's Dictionary of Plastics, Third Edition, pp. 434-435.

(Continued)

*Primary Examiner*—Kevin C. Sirmons
*Assistant Examiner*—Laura C. Schell
(74) *Attorney, Agent, or Firm*—INCAPLAW; Terrance A. Meador

(57) ABSTRACT

A fluid warming cassette useful in a system for warming parenteral fluids is provided. The cassette comprises a thermally conductive, flexible fluid container with a fluid channel. Rails are disposed in the fluid container near its periphery, and a stiffener is disposed in the fluid container, between the rails, near an end of the cassette. Together, the rails and stiffener impart structural rigidity to the fluid container. The fluid container, rails and stiffener are joined into an integrated structure useful as a fluid warming cassette. One or more of the rails has a multilateral shape to key the cassette for insertion into a fluid warming unit.

33 Claims, 6 Drawing Sheets

U.S. PATENT DOCUMENTS

| | | | |
|---|---|---|---|
| 5,098,202 A | 3/1992 | Rosenbaum | 383/67 |
| 5,102,234 A | 4/1992 | Levy | 383/38 |
| 5,106,373 A | 4/1992 | Augustine et al. | 604/113 |
| 5,125,069 A | 6/1992 | O'Boyle | 392/465 |
| 5,205,348 A * | 4/1993 | Tousignant et al. | 165/46 |
| 5,245,693 A | 9/1993 | Ford et al. | 392/470 |
| 5,254,094 A | 10/1993 | Starkey et al. | 604/113 |
| 5,381,510 A | 1/1995 | Ford et al. | 392/470 |
| 5,423,421 A | 6/1995 | Inoue et al. | 206/219 |
| 5,520,975 A | 5/1996 | Inoue et al. | 428/35.9 |
| 5,733,619 A | 3/1998 | Patel et al. | 428/36.91 |
| 5,792,526 A | 8/1998 | Watanabe et al. | 428/35.7 |
| 5,865,309 A | 2/1999 | Futagawa et al. | 206/219 |
| 5,875,282 A * | 2/1999 | Jordan et al. | 392/470 |
| 6,175,688 B1 | 1/2001 | Cassidy et al. | 392/470 |
| 6,464,666 B1 | 10/2002 | Augustine et al. | 604/113 |
| 6,535,689 B2 | 3/2003 | Augustine et al. | 392/470 |
| 6,608,968 B2 * | 8/2003 | Bakke | 392/470 |
| 6,673,098 B1 | 1/2004 | Machold et al. | 607/96 |
| 6,775,473 B2 | 8/2004 | Augustine et al. | 392/470 |
| 6,901,216 B2 * | 5/2005 | Jusiak et al. | 392/470 |
| 7,010,221 B2 | 3/2006 | Augustine et al. | 392/470 |
| 2002/0081109 A1 | 6/2002 | Mitsunaga et al. | 392/470 |
| 2002/0193739 A1 | 12/2002 | Augustine et al. | 604/113 |
| 2003/0077079 A1 | 4/2003 | Entenman et al. | 392/470 |
| 2004/0026068 A1 | 2/2004 | Schmidt | 165/46 |
| 2004/0190885 A1 | 9/2004 | Entenman et al. | 392/470 |
| 2007/0173759 A1 | 7/2007 | Augustine et al. | 604/113 |

FOREIGN PATENT DOCUMENTS

| | | |
|---|---|---|
| EP | 0 096 191 | 4/1983 |
| EP | 0 119 469 | 9/1984 |
| EP | 0 206 416 | 6/1986 |
| WO | WO 93/10416 | 5/1998 |
| WO | WO 00/53246 | 9/2000 |
| WO | WO 01/26719 | 4/2001 |

OTHER PUBLICATIONS

Medi-Temp II Blood/Fluid Warmer, Product Bulletin.
Written Opinion mailed Jul. 27, 2001 for PCT Application PCT/US00/02630, published as WO 01/26719.
IPER mailed Jan. 11, 2002 for PCT Application PCT/US00/02630, published as WO 01/26719.

* cited by examiner

FLUID WARMING CASSETTE WITH RAILS AND A STIFFENING MEMBER

RELATED APPLICATIONS

Four commonly-owned U.S. patent applications with related subject matter include the following:

Ser. No. 10/210,643, filed Jul. 31, 2002 for "Intravenous Fluid Warming Cassette with Stiffening Member and Integral Handle", published as US 2002/0193739 on Dec. 19, 2002, now U.S. Pat. No. 7,010,221, issued Mar. 7, 2006;

Ser. No. 10/214,966, filed Aug. 8, 2002 for "Fluid Warming Cassette with Tensioning Rod", published as US 2004/0026068 on Feb. 12, 2004, now U.S. Pat. No. 7,232,457, issued Jun. 19, 2007;

Ser. No. 10/304,809, filed Nov. 25, 2002 for "IV Fluid Warming System with Detection of Presence and Orientation of an IV Fluid Heat Exchanger", published as 2003/0077079 on Apr. 24, 2003, now U.S. Pat. No. 6,775,473, issued Aug. 10, 2004; and Ser. No. 10/397,942; filed Mar. 25, 2003 for "Fluid Warming Cassette and System Capable of Operation under Negative Pressure", published as 2004/0190885 on Sep. 30, 2004.

These four patent applications are incorporated herein by this reference.

In addition, the following commonly-owned U.S. patent applications with related subject matter are currently pending:

Ser. No. 11/257,831, filed Oct. 25, 2005 for "Intravenous Fluid Warming Cassette with Stiffening Member and Integral Handle", published Jul. 26, 2007 as US 2007/173759;

Ser. No. 11/818,880, filed Jun. 15, 2007 for "Fluid Warming Cassette and System Capable of Operation under Negative Pressure;

Ser. No. 11/789,515, filed on Apr. 24, 2007 for "Heat Exchanger for High Flow Rate Infusion";

Ser. No. 11/789,523, filed on Apr. 24, 2007 for "High Flow Rate Infusion Unit and Heat Exchanger"; and, Ser. No. 11/789,752, filed on Apr. 24, 2007 for "Bubble Trap for High Flow Rate Infusion".

BACKGROUND

This invention is generally related to parenteral fluid warming systems and, more particularly, to the structure of a fluid warming cassette used with a warming apparatus, in which the structure of the cassette includes a fluid container with rails and a stiffening member near the proximal end of the cassette.

Fluid warming apparatuses, designed to warm and administer parenteral fluids and blood products (hereinafter "fluids"), are in common use. Generally, such fluids are heated and administered using fluid warming systems. A parenteral fluid warming system usually includes a warming unit into which a fluid warming cassette is placed. The fluid warming cassette includes a fluid container with a structure designed for handling and for being received and supported in the warming unit. The fluid container includes a fluid channel and is typically made of plastic film material and/or thin metal.

In use, the cassette is placed into the warming unit to heat the fluids as they flow through the fluid channel. Heat is transferred to the fluid through the fluid container from a heat source such as heated metal plates, heated liquid, or heated gas. Metal plate, "dry heat" exchanger warming units are widely known.

In such systems, heat transfer from the warming unit to the fluid warming cassette is typically by conduction, with the heat source including, for example, one or more metal plates brought into contact with the warming cassette. There are systems that operate by conduction between a bath of heated water and a fluid warming cassette; some systems use induction for heating; others use micro-waving means. Still other systems operate by convection, disposing a fluid warming cassette in a flow of heated air. Those skilled in the art will appreciate that heat transfer in such systems is a complex process that actually compounds conduction, radiation, and convection. Therefore, characterization of a mode of heat transfer to a fluid warming cassette actually denotes the principal mode of transfer and does not necessarily exclude contribution by one or more additional modes.

To increase the thermal efficiency and temperature responsiveness of a fluid warming system in which a fluid warming cassette is disposed for conductive heat transfer from warming plates, the distance between the heater plates is usually very small. This implies that a fluid warming cassette should be a thin, flat container, constructed from selected materials. Plastic film materials are commonly used in the manufacture of disposable fluid warming containers. Such designs are disclosed in the four above-referenced patent applications.

Since these fluid containers are thin, it would be difficult to insert one into a conductive warming unit simply by sliding it between the warming plates. The container may kink or tear when being slid into or out of such a narrow space. As a result, the fluid container needs some type of structural support, usually a frame, although a tensioning rod may also be used. A frame stiffens the fluid container so that the fluid warming cassette can be handled, and also inserted into and removed from the warming unit. Together, the fluid container and frame constitute a fluid warming cassette, a modular unit of equipment designed to be received in, or inserted into, a larger warming unit. A flexed tensioning rod disposed in a fluid container exerts a tension between the sides of the container thereby imparting the desired stability and handleability to a fluid warming cassette.

A frame for a fluid warming cassette comprehends numerous elements, including a quadrilateral frame structure with a handle portion that extends outside of the warming unit when the cassette is seated in the unit in order to provide something that can be grasped to manipulate the cassette for insertion and extraction. The frame type of construction adds steps to the process for manufacturing fluid warming cassettes, leading to lower yields and higher manufacturing costs. In this regard, the frame is preferably made by a vacu-form process which can yield frames with dimensional variations that are not accommodated by the narrow space between warming plates. Relatively expensive materials must be used for tensioned rods in order to achieve acceptable shelf lifetimes for fluid warming cassettes which incorporate them.

It would be advantageous if a simplified, effective, low cost fluid warming cassette were made available for a parenteral fluid warming system in which the cassette is received between heating plates of a warming unit for conductive heat transfer therefrom.

It would be advantageous if a fluid container could be invested with enough stiffness for insertion between close-set warming plates of a warming unit, yet be thin enough to efficiently transfer heat by conduction from the plates to the fluid, without the requirement of an expensive frame.

It would be advantageous if the fluid warming cassette were provided with a keying mechanism that prevents it from being inserted either upside down, or backwards in a warming unit.

SUMMARY

A fluid warming cassette useful in a system for warming parenteral fluids is described. The cassette comprises a thermally conductive, flexible fluid container with a fluid channel. Rails are disposed in the fluid container near its periphery, and a stiffener is disposed in the fluid container near an end of the cassette. Together, the rails and stiffener impart structural rigidity to the fluid container. The fluid container, rails and stiffener cooperate to provide an integrated structure called a "fluid warming cassette" or, simply, a "cassette".

The rails are elongate members that impart longitudinal stiffness to the fluid container. They are also shaped and positioned to act as a keying mechanism, preferably one constituted of lands, which orients the cassette with respect to a counterpart mechanism in a fluid warmer to prevent incorrect insertion of the cassette into the warmer.

The stiffener may include a relatively stiff, shaped planar member lying between the rails near an end of the fluid container that imparts transverse stiffness to the fluid container. The stiffener and its disposition provide a flat, relatively stiff handle portion at the end of the cassette for being grasped so that the cassette may be manipulated for insertion into and extraction from a warming unit.

Inlet and outlet ports to the fluid channel are provided on the fluid container, at respective ends of the channel.

When the cassette is oriented for use with a warming unit, one end faces a thin laminar space in the unit. With the cassette oriented so that the rails engage corresponding grooves in the warming unit space, the cassette may be pushed into the warming unit. Then, fluid flows through a tube into the fluid channel, where it is heated by the warming unit, and out of the cassette through another tube for delivery.

DETAILED DESCRIPTION

A fluid warming cassette is intended for use with a fluid warming unit to warm fluids for intravenous infusion. For example, the cassette may be used with a "dry heat" warming unit in which heater plates are disposed in an opposing, spaced-apart configuration, separated by a thin laminar space. In this case, the cassette is received in the space between the heater plates, in close contact with the heater plates for transfer of heat by conduction from the plates to the cassette.

The fluid warming cassette includes a fluid container. Rails are disposed in the fluid container near its periphery, and a stiffener is positioned in the fluid container near a proximal end of the cassette. The fluid container is made of two or more sheets of thermally conductive plastic film material. The sheets of plastic film material are bonded or otherwise joined in a pattern which creates a fluid channel between the sheets. A fluid channel with a serpentine pattern is illustrated, although other patterns are contemplated. Preferably each of the plastic sheets is a film 0.1 mm thick, or less. The rails are elongate members, with at least one of the rails having a multi-lateral shape in cross section to provide keying of the cassette with respect to one or more counterpart grooves in a warming unit. A handle portion of the fluid warming cassette is constituted of the stiffener and a portion of the fluid container which sandwiches the stiffener, near a proximal end of the cassette.

Figure 1:
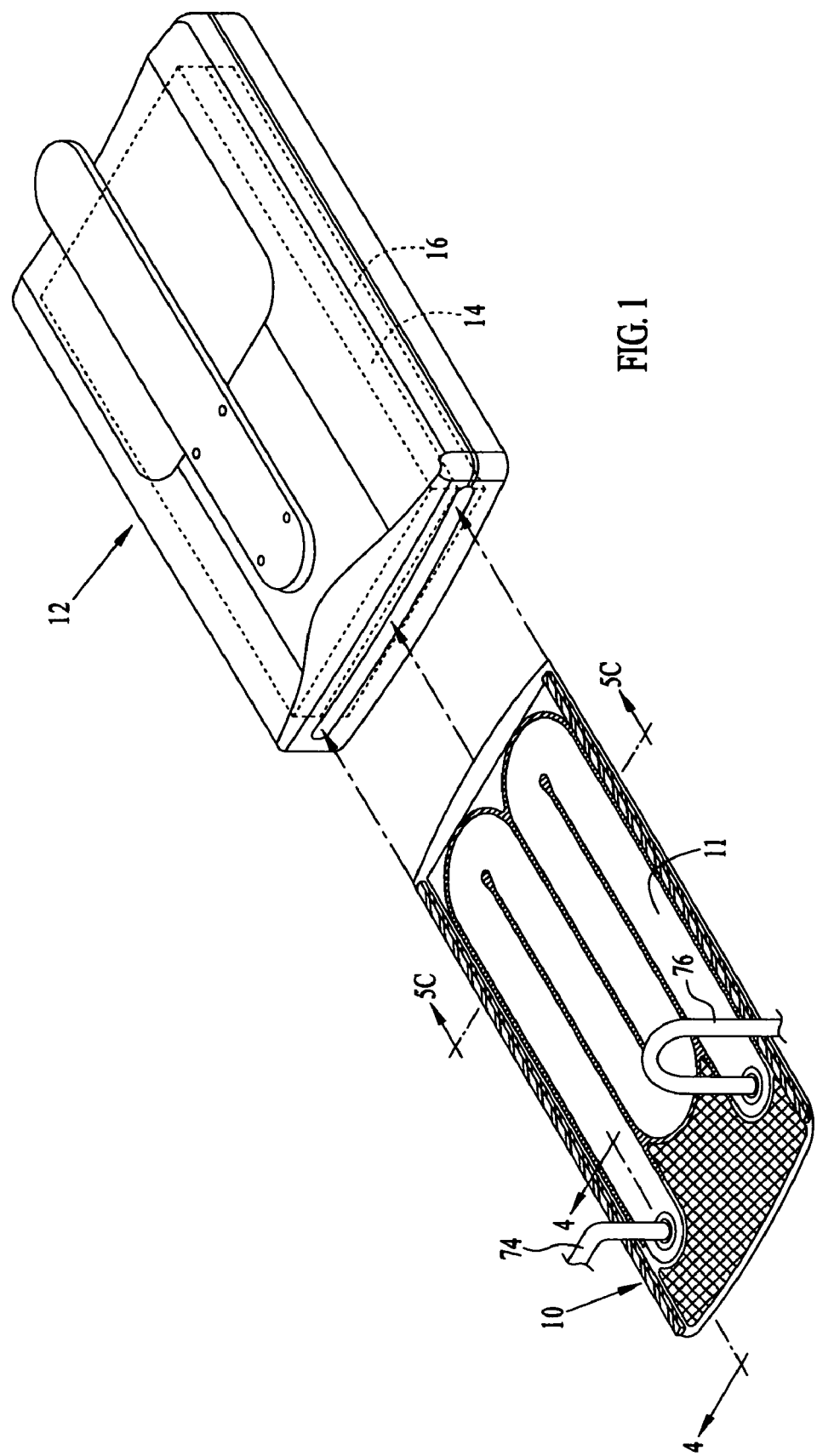
FIG. 1 is a perspective view of a fluid warming cassette according to this invention disposed for use with a fluid warming unit.

FIG. 1 is a perspective illustration of a fluid warming cassette 10 with a fluid channel 11 according to the invention for use with a fluid warming unit 12. The warming unit 12 is a "dry heat" unit with warming plates 14 and 16. The plates 14 and 16 are spaced apart at a fixed distance, and the cassette 10 is inserted between the plates 14 and 16 so that the fluid in the cassette 10 is heated by conduction from the plates 14 and 16 before infusion into a body. Alternately, the cassette could be warmed by convection in a stream of heated air, or by conduction in a bath of heated fluid.

Figure 2:
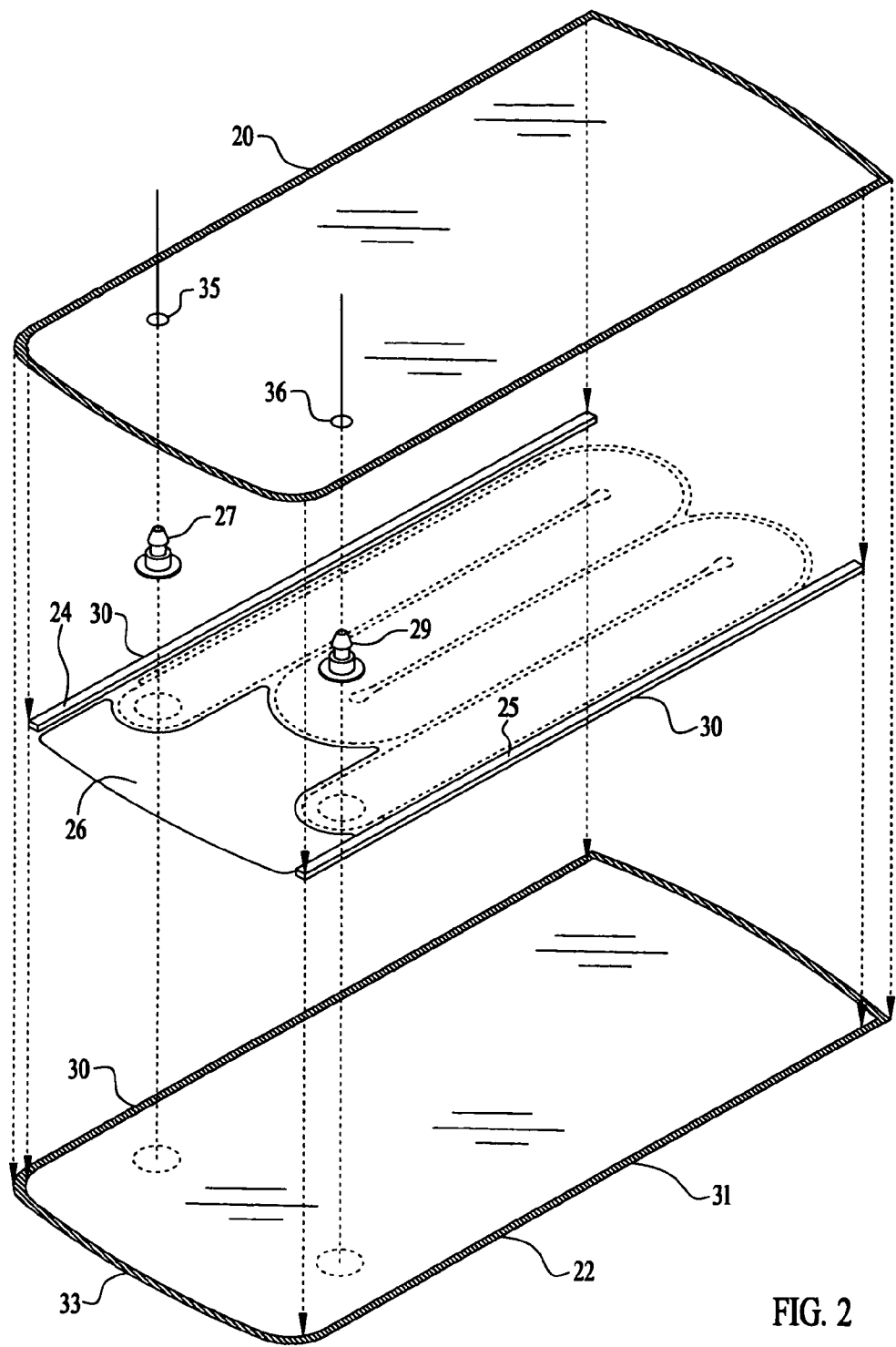
FIG. 2 is an exploded view of the fluid warming cassette of FIG. 1.
Figure 3:
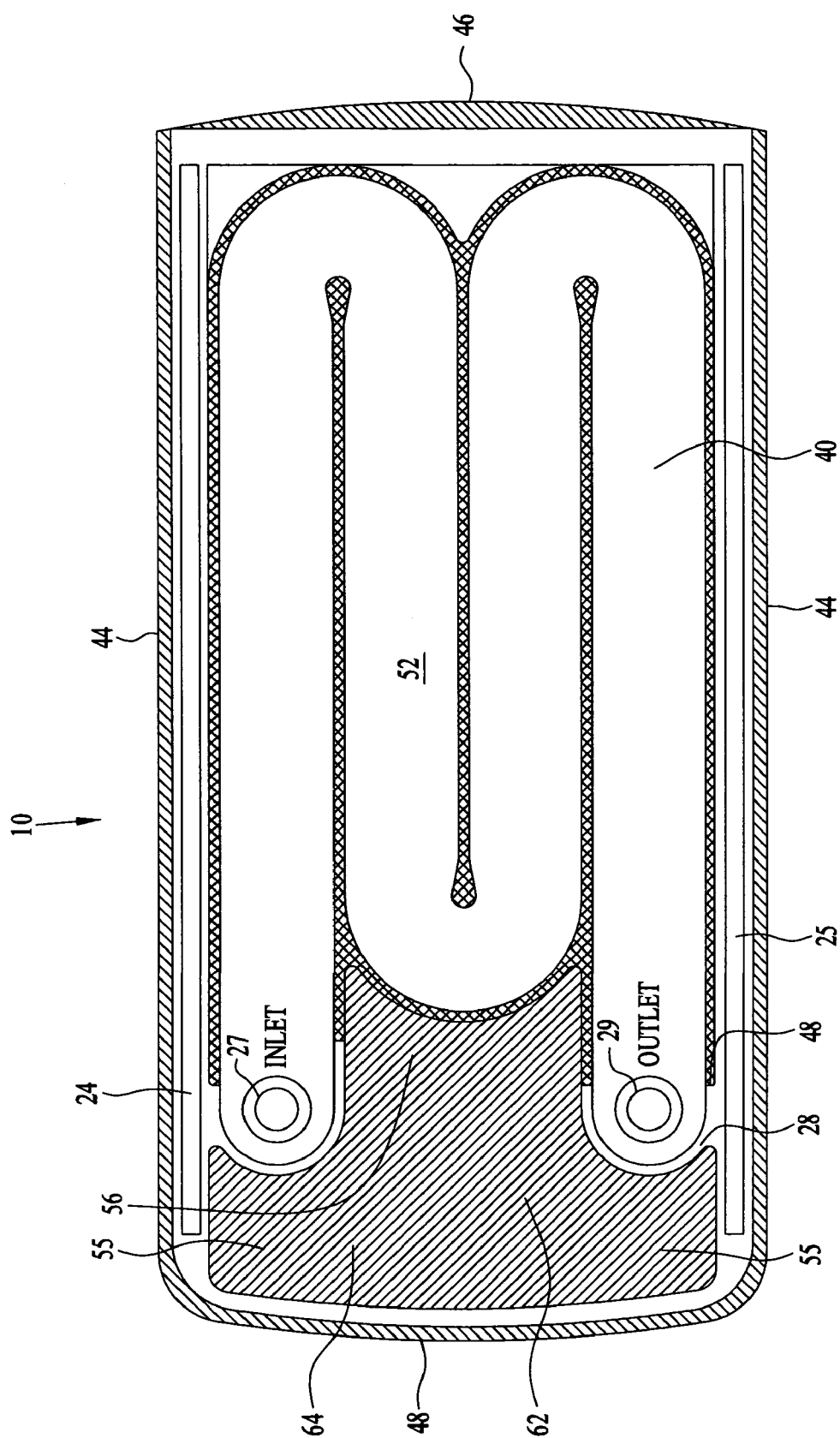
FIG. 3 is a more detailed depiction of the fluid warming cassette of FIG. 1.

Refer now to FIGS. 2 and 3, in which FIG. 2 is an exploded view of the fluid warming cassette 10 of FIG. 1 showing its elements, and FIG. 3 is a top plan view of the assembled cassette. The cassette 10 includes a first (or "covering") sheet 20, a second (or "base") sheet 22, a first rail 24, a second rail 25, a stiffener 26 that is separate from the rails 24, 25, and two ports 27, 29. The rails 24, 25 are flexible or semi-rigid filaments, members or structures, each having the shape of a thin, substantially straight piece with a multi-lateral (preferably, polygonal, trapezoidal or rectangular) cross section. The corners of the selected shape may be pointed, rounded, of flattened. The stiffener 26 is a planar piece of relatively stiff material having a shape, in plan, that extends between the rails, and that may also extend toward, and up to, the fluid channel. The ports are molded plastic fitments.

During a process of making the cassette, the rails 24, 25 are parallel with each other and aligned with respective edges 30 and 31 of the base sheet 22, while the stiffener 26 is aligned with an end 33 of the base sheet, and disposed transversely between the rails. The ports 27, 29 are received in respective openings 35, 36 in the covering sheet 20 and joined by flange welds, at their bases, to the inner surface of the covering sheet 20 which faces the base sheet 22. To assemble the cassette shown in FIGS. 1-3, the sheets 20 and 22 are aligned with each other and the other parts, and a heat sealing platen, RF platen, or US horn is applied, thus forming the fluid container 40 by joining the sheets by seals within and around their peripheries to form a periphery of the cassette including sides 44, distal end 46 and proximal end 48 (see FIG. 3). The rails 24, 25 are sandwiched between the sheets and disposed near, within, or against the sides 44, and the stiffener 26 is sandwiched between the sheets and disposed near, within or against the proximal end 48. Between the rails 24, 25, and between the stiffener 26 and the distal end 46, the first sheet 20 and second sheet 22 are fused or welded together in a fluid channel pattern to form the fluid channel 52. The stiffener has an elongate portion 55 that extends between the rails 24, 25 and reaches from the proximal end 48 and may include a secondary portion 56 that protrudes toward, or up to, the fluid channel 52.

As best seen in FIG. 3, the fluid container 40, which is substantially planar, or flat, before use, is generally disposed in a flat or laminar space. The rails 24, 25 stiffen the fluid container 40 longitudinally within the flat or laminar space, while the stiffener 26 stiffens the fluid container transversely within the flat or laminar space, between the rails near the proximal end 48. Together, the rails 24, 25 and the stiffener 26 impart enough rigidity to stiffen the fluid container 40, thereby enabling the cassette 10 to support itself in a generally planar condition while being handled, inserted, extracted or otherwise used or manipulated as a single modular unit. However, since the rails and stiffener are not joined to each other, no frame has to be fabricated, nor any rod flexed, thereby simplifying the fabrication of the cassette.

As best seen in FIGS. 1 and 3, the ports 27, 29 are in fluid communication with respective ends of the fluid channel 52. Preferably, the ports are upright or perpendicular to the fluid container 40. With the ports so disposed, one port functions as an inlet port for conducting fluid into the fluid channel 52, while the other acts as an outlet port for conducting warmed fluid out of the fluid channel. In the example illustrated in FIG. 3, the port 27 is the inlet port, and the port 29 is the outlet port, although this relationship may be reversed in view of design considerations.

Figure 4:
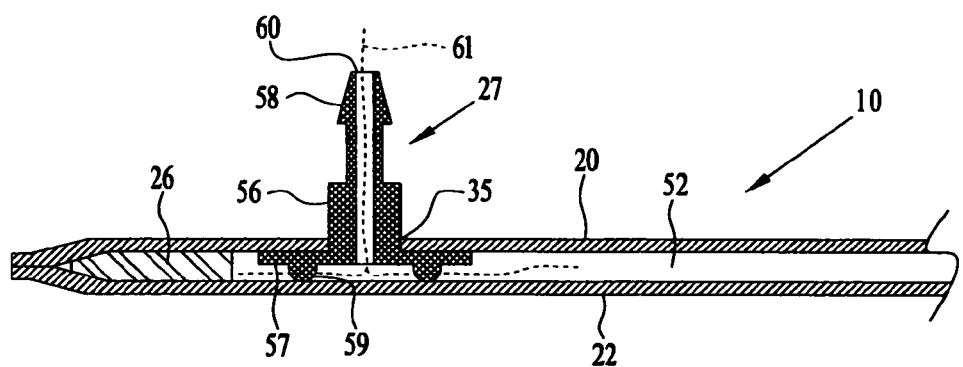
FIG. 4 is a partial sectional view showing a port in the cassette.

FIG. 4 is an enlarged sectional view of the cassette taken along lines 4-4 of FIG. 1. This figure shows the port 27 in fluid communication with a respective end of the fluid channel 52; it is illustrative also of the structure of the port 29 in the fluid channel 52. As described previously, the first sheet 20 includes holes 35, 36 dimensioned such that the upstanding portion 56 of the inlet 27 and outlet 29 ports extend through the first sheet 20, the disk shaped base 57 preventing the ports from coming out. Tubes (not shown) may be attached to the barbed end 58. The disk shaped base 57 may include a plurality of bumps 59 on the bottom surface of the base 57. Alternatively, grooves may be used instead of the bumps. The grooves or bumps prevent the second sheet 22 from completely covering the fluid hole 60 during use. Dotted line 61 shows the fluid flow path into or out of the fluid warming cassette 10.

The proximal end 48 provides a handle portion 64 of the fluid warming cassette. The handle portion 64 is generally the portion of the fluid container 40 near the proximal end 48 of the cassette which sandwiches the elongate portion 55 of the stiffener 26. The handle portion 64 is provided to accommodate finger purchase. When the cassette 10 is engaged with warming device 12 (see FIG. 1), the handle portion 64 is not received (at least, not entirely received) between the plates 14 and 16. The handle portion 64 remains accessible outside of the warming unit while the rest of the cassette is being heated between plates 14 and 16. Either or both of the first and second sheets 20 and 22 may be bonded, joined, or sealed to some of or the entire stiffener. Alternatively, the stiffener may be left free in the space between the sheets. The first case imparts more stiffness to the cassette, but is more difficult to manufacture than the second.

The handle portion 64 provides a label surface area 62 which may be used for labeling (see FIG. 3). Since the majority of the cassette 10 is inside the warming unit during use, it is convenient to have labeling visible to the user even during use. The handle portion 64 is always external to the warming unit and, therefore, is an ideal platform for such labeling. In addition, the handle portion 64 may include a mechanism for supporting fluid inlet and fluid outlet tubing, and providing strain relief preventing undue tension being applied to the tubing. Without this kind of strain relief, there is the risk of tension on the tubing, resulting in tearing the plastic film material. Attaching the tubes helps to prevent kinking of the tubing as it leaves the warming unit.

The rails 24, 25 may each be a filament formed from a material selected from the group consisting of polyolefin, polyethylene, polypropylene, polyvinyl chloride (PVC), and polyurethane, or any other equivalent plastic capable of providing the appropriate stiffness to the cassette. Other suitable rail materials include spring steel, aluminum, and any suitable metal capable of providing the appropriate stiffness. In addition, composite materials may be used for the rails 24, 25. For example, the rails may be similar in construction to a composite fishing pole, made from fiberglass or other composite materials capable of providing the appropriate stiffness. The rails can be manufactured by extrusion, die cutting, injection molding, thermal processes or other processes compatible with the materials selected. The rails not only stiffen the cassette, they also provide a keying mechanism requiring proper orientation of the cassette 10 with respect to the warming plates of the warming unit 12. One preferred shape for each rail is that of a rectangle in order that the rails may also constitute lands on the cassette that are received in corresponding grooves of the warming plates.

The planar stiffener 26 is preferably constituted of a high density polyethylene (HDPE) material of non specific color. Other materials of which the stiffener may be formed include other stiff synthetic plastic materials such as polycarbonate, ABS, PVC, and other equivalents, various metals, and cardboard or card stock. The stiffener is preferably about 0.75 mm in thickness, although a thickness in the range of 0.35 to 1.5 mm is useful. The factors influencing the thickness of the stiffener include the stiffness of the material of which it is made, the thicknesses of the first and second sheets, and the thickness of the space into which the cassette must fit.

The first sheet 20 and second sheet 22 which are joined to form the fluid container 40 may be made from one or more materials selected from the group consisting of polyester, polyamide (Nylon®, DuPont), polyethylene glycol terephthalate (Mylar®, DuPont), metal foils, ionomer resins (Surlyn®, DuPont), polyolefin (polyethylene, polypropylene), polyvinyl chloride (PVC), polyurethane, and ethyl vinyl acetate (EVA) co-polymer.

The fluid container 40 includes the fluid channel 52 and at least a first port in fluid communication with a first end of the fluid channel 52, which is outlined with cross-hatched lines in FIG. 3. When the fluid warming cassette is deployed for use, a first tube 74 is joined to the first port 27. The fluid container 40 also includes a second port 29 in fluid communication with a second end of the fluid channel 52. A second tube 76 is joined to the second port 29.

As discussed, the handle portion 64 may include a label surface area 62, highlighted with cross-hatched lines in FIG. 3. In the preferred embodiment, labeling may be printed directly on the label surface area 62, eliminating the need for a separate label. In addition, labeling may be printed anywhere in the upper or lower sheets and may be printed before, or after, the sheets are attached together. In another embodiment, the cassette 10 may receive a label (not shown) overlying the label surface area 62. The label can be visible to the eye, or configured for electronic identification, such as a bar code. It is also contemplated that a label may be applied or printed directly on the stiffener.

Figure 5A:
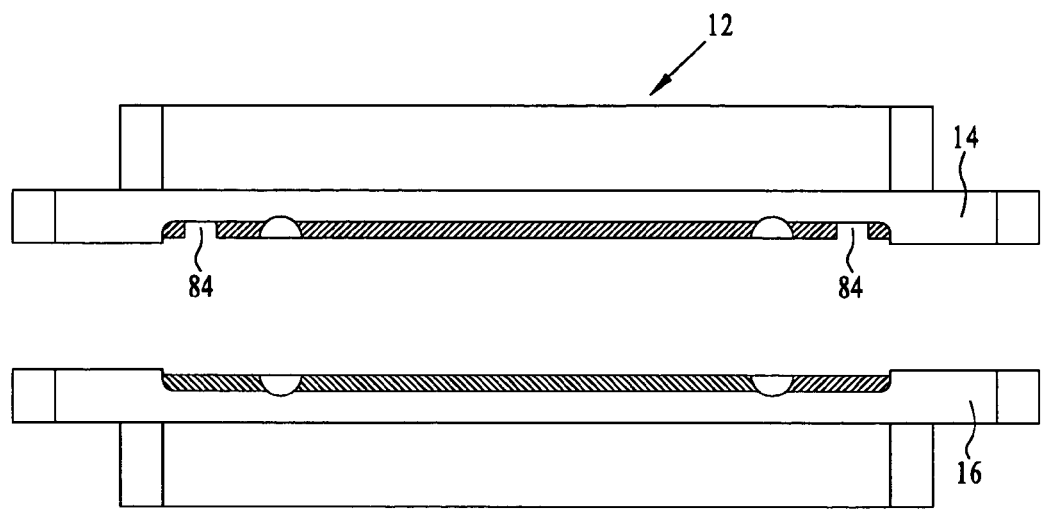
FIGS. 5A through 5C illustrate details of a keying mechanism used to selectively orient the fluid warming cassette in the fluid warming unit.
Figure 5B:
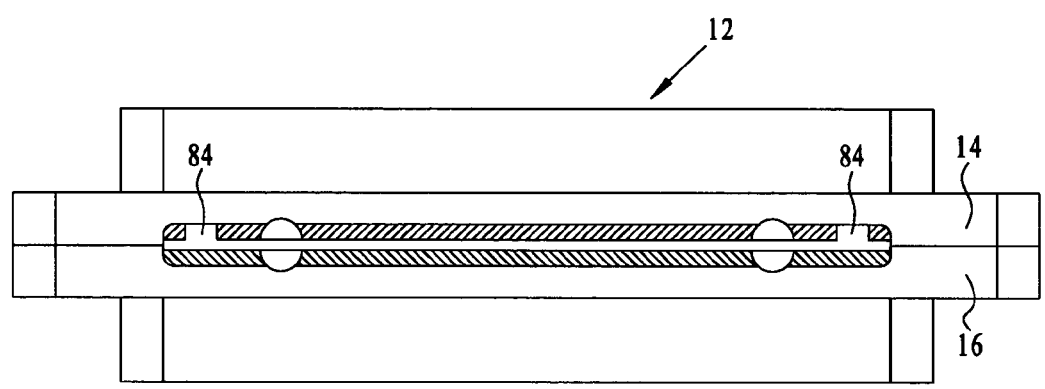
Figure 5C:
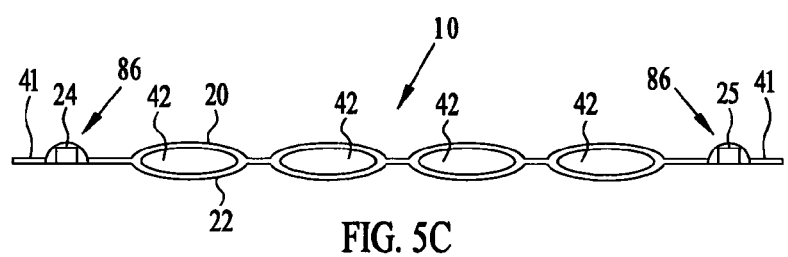

FIGS. 5A through 5C illustrate elements of an illustrative keying mechanism used to orient the cassette 10 in the warming unit 12. The warming unit 12 includes the first and second opposing warming plates 14 and 16, adapted to accept the warming cassette 10 in a correct orientation. FIG. 5A is a simplified end view of the warming unit 12. The warming plates 14 and 16 have been separated for the purpose of clarifying the keying mechanism. Two grooves 84 are formed in the upper plate 14 to cooperate with the elements of the keying mechanism on the fluid warming cassette 10. FIG. 5B illustrates the warming unit 12 with the warming plates 14 and 16 assembled for normal operation. Although this example shows keying with reference to the upper plate 14, one may also key with lands referenced to the lower plate 16. Further, cassette keying can be accomplished using a single land and a single groove.

FIG. 5C is a sectional view of the cassette taken along 5C-5C of FIG. 1. These figures illustrate an embodiment of the fluid warming cassette in which the rails 24, are positioned within the cassette 10 to act as rectangular lands 86 with respect to the grooves 84 to mate the cassette 10 with the warming plates in a predetermined correct orientation. In this regard, each of the rails 24, 25 has a first surface that supports an arch of the first sheet 20, and a second surface that is flush with the base sheet 22. When the cassette is inserted in the correct orientation between the warming plates, the arched portion of the first sheet conforms to the complementary rectangular shapes of the lands and grooves.

The cassette 10 may also include a stop mechanism. In the example shown in FIGS. 1-3, the inlet and outlet ports 27 and 29, perpendicular to the fluid container 40 between the rails near the proximal end 48, limit the extent to which the cassette 10 may be inserted between the warming plates 14, 16.

Figure 6:
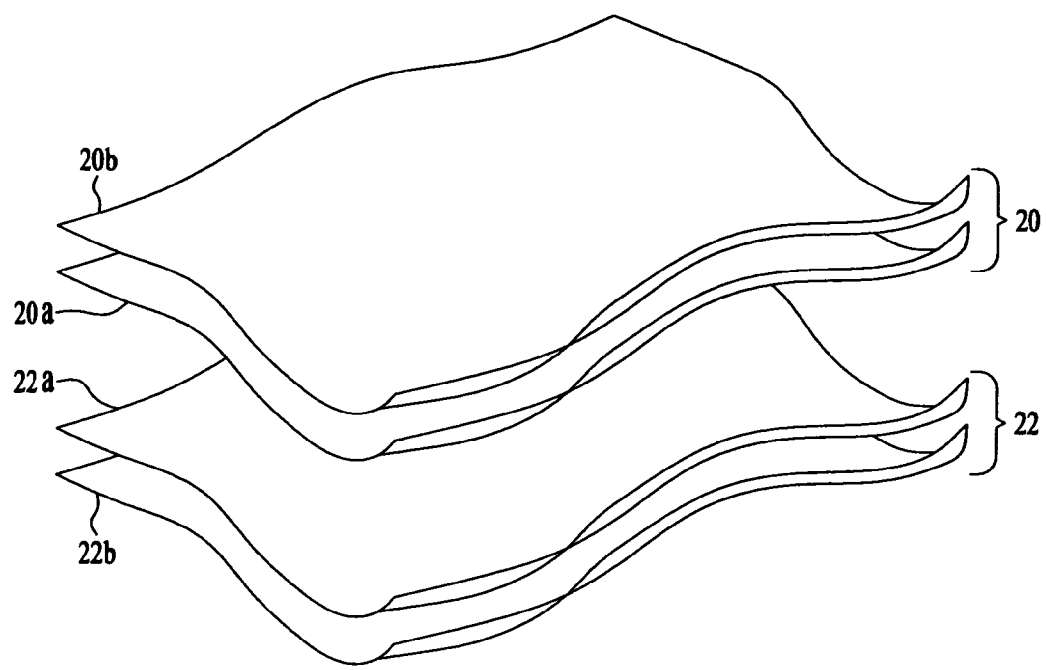
FIG. 6 illustrates a multi-layer construction for first and second sheets of the fluid container.

In some cases, a multi-layer construction provides advantages such as tailoring the sheets of which the fluid container is formed for optimum strength so that the container can accommodate substantial fluid pressures, such as those encountered with use of an IV pump. A multi-layer construction is disclosed in applicants U.S. patent application Ser. No. 09/415,558 filed on Oct. 8, 1999, which is incorporated in its entirety by this reference. In an alternative construction, the first sheet 20 or the second sheet 22, or both, may have a multi-layer construction. As shown in FIG. 6, each sheet could include an inner thermo-sealable layer 20a, 22a and a outer structural layer 20b, 22b. The structural layer may be selected from the group of materials consisting of polyester, polyamide (Nylon®, DuPont), polyethylene glycol terephthalate (Mylar®, DuPont), metal foils, and ionomer resins (Surlyn®, DuPont). The thermo-sealable layer may be selected from the group of materials consisting of polyolefin, polyethylene, polypropylene, polyvinyl chloride (PVC), polyurethane, and ethyl vinyl acetate (EVA) co-polymer. Many techniques are contemplated for bonding the layers of a multi-layered sheet to create a laminated structure. These include adhesive bonding the layers, thermal bonding the layers and extruding a molten layer of one material directly onto a layer of another material layer ("extrusion coating").

Refer to FIG. 6. The first sheet 20 is shown, including a plurality of flexible film layers; two layers 20a and 20b of the first sheet shown. The second sheet 22 includes a plurality of layers, with layers 22a and 22b of the second sheet being shown. A construction of the warming cassette 10 with multi-layer sheets is similar to previously disclosed with reference to FIG. 2.

In another embodiment, the top 20 and bottom 22 sheets are constructed using materials with a low coefficient of friction. In a multi-layer sheet design, the outside layers 20b, 22b of sheets 20 and 22, respectively are constructed using materials with a low coefficient of friction. The lower coefficient of friction permits the fluid warming cassette 10 to be more easily inserted between warming plates 14 and 16 (see FIG. 1).

The fluid warming cassette 10 can be inserted into the warming unit 12 by a user grasping the handle portion 64, orienting the warming cassette 10 so that the lands 86 are aligned with the grooves 84, inserting the distal end 46 between the plates 14 and 16 and sliding the warming cassette 10 inwardly between the plates 14 and 16 until the stopping mechanism 27, 29 halts further insertion.

Figure 7:
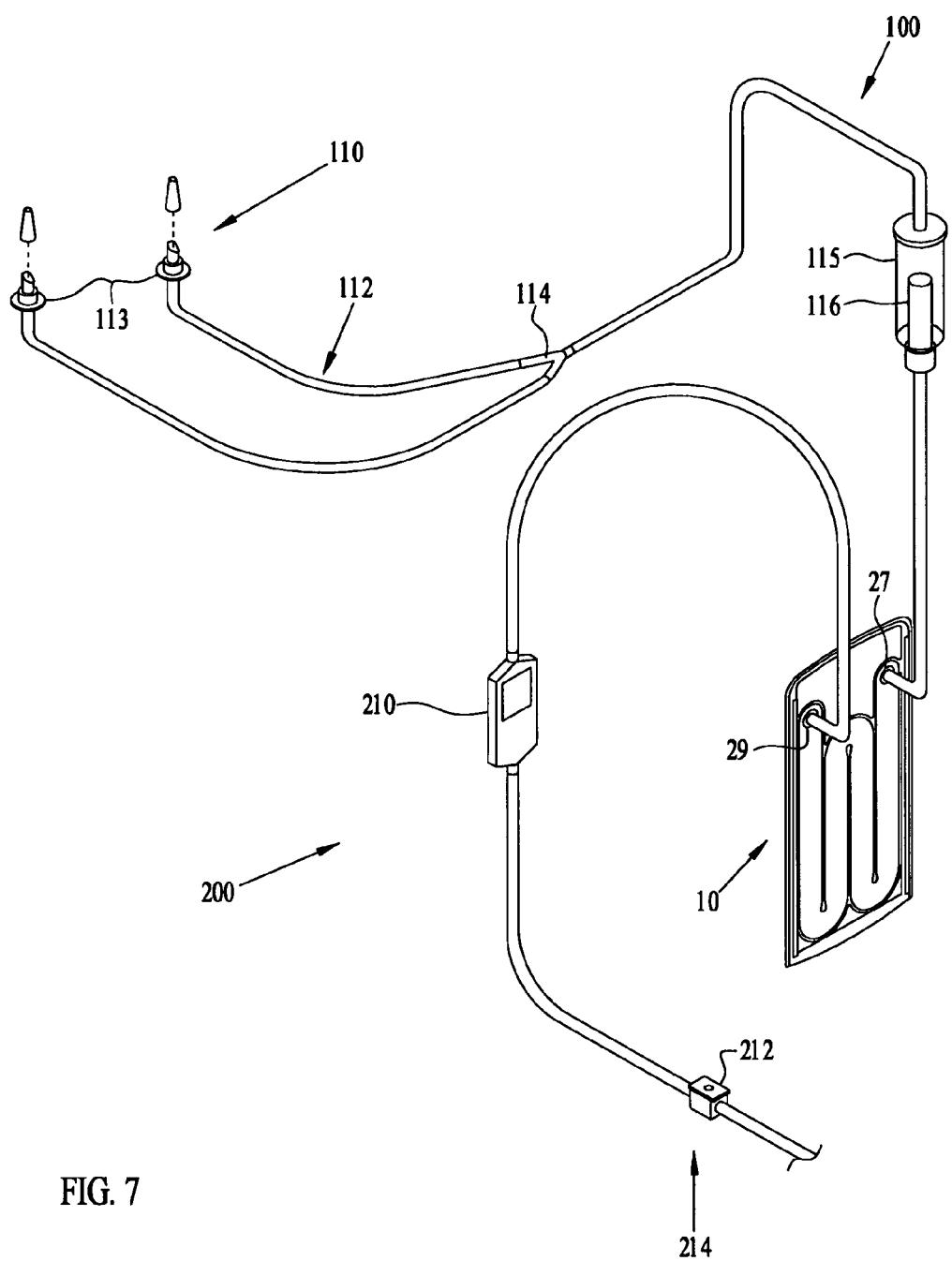
FIG. 7 is a block diagram of a fluid warming system kit including the fluid warming cassette of FIGS. 1-4 and 5C.

A fluid warming kit is illustrated in FIG. 7. The kit includes a fluid warming cassette 10 with rails and a stiffener as described above. An inlet line 100 is connected to the inlet port 27. An outlet line 200 is connected to the outlet port 29. The inlet line 100 is for receiving and conducting fluid from a source to the cassette for warming thereby. The outlet line 200 is for conducting warmed fluid from the cassette to an application site. Both the inlet line and outlet line include a series of elements in which an element is coupled to one or more other elements by a length or lengths of tubing; such lengths of tubing may or may not include other elements; such other elements may be attached to the tubing, or may join lengths of tubing. Thus, the inlet line 100 has an inlet end 110, which may include a Y-branch 112 for receiving fluid from one or more sources through spikes 113. The Y-branch is coupled through a 3-way connector 114 to the inlet of a drip chamber 115 with a filter 116. The drip chamber has an outlet coupled to the inlet port 27. In the outlet line 200, the outlet port 29 is coupled to the inlet of a self-venting bubble trap 210. The outlet of the bubble trap is connected to an injection site 212 where medicaments can be added to a stream of warmed fluid. The injection site 212 is coupled to an outlet end 214 of the outlet line.

Other variations and embodiments of the fluid warming cassette will occur to those skilled in the art with reflection upon the disclosed examples. The only limitations on the scope of exclusive rights to the inventions described are in the following claims.

We claim:

1. A fluid warming cassette, comprising:
   a first sheet and a second sheet joined together to form a fluid container with a periphery, the periphery having a proximal end, a distal end and first and second sides there between;
   a fluid channel in the fluid container between the first sheet and the second sheet;
   first and second rails disposed between the first sheet and second sheet, inside the periphery, near the first and second sides, respectively; and
   a planar stiffener near the proximal end, separate from the first and second rails, disposed between the first sheet and the second sheet, and extending between the rails for substantially the width of the fluid container from near the first rail to near the second rail.

2. The fluid warming cassette of claim 1 in which each of the first and second rails has a multi-lateral cross-section.

3. The fluid warming cassette of claim 2, in which each of the first and second rails has a first surface supporting a respective arch of the first sheet and a second surface, opposite the first surface and flush with the second sheet.

4. The fluid warming cassette of claim 1 in which the stiffener has a first elongate portion extending between the first and second rails and a second portion protruding from the first portion in the direction of the distal end.

5. The fluid warming cassette of claim 4 in which the fluid channel is disposed between the first and second rails, and between the second portion and the distal end.

6. The fluid warming cassette of claim 1, further including a handle portion in the proximal end constituted of the first and second sheets sandwiching the stiffener.

7. The fluid warming cassette of claim 6 in which the stiffener has a first elongate portion extending between the first and second rails and a second portion protruding from the first portion toward the fluid channel.

8. The fluid warming cassette of claim 6 in which the handle portion includes a label surface.

9. The fluid warming cassette of claim 1 further including first and second ports in fluid communication with the fluid channel.

10. The fluid warming cassette of claim 9 in which the first and second ports are disposed perpendicularly to the fluid container.

11. The fluid warming cassette of claim 10 in which the first and second ports constitute a cassette insertion stop.

12. The fluid warming cassette of claim 1 in which the rails are made from a material selected from the group consisting of polyvinyl chloride (PVC), polyurethane, polyolefin, polypropylene, polyethylene, polyester, and other polymeric materials.

13. The fluid warming cassette of claim 1 in which the rails are made from a material selected from the group consisting of spring steel, aluminum, and other metallic materials.

14. The fluid warming cassette of claim 1 in which the rails are made from a composite material.

15. The fluid warming cassette of claim 1 in which the stiffener is made from high density polyethylene.

16. The fluid warming cassette of claim 1 in which the stiffener is made from a material selected from the group consisting of polycarbonate, ABS and PVC.

17. The fluid warming cassette of claim 1 in which the stiffener is made from cardboard or card stock.

18. The fluid warming cassette of claim 1 in which the stiffener is made from metal.

19. The fluid warming cassette of claim 1 in which the first sheet and second sheet are made from a material selected from the group consisting of polyester, polyamide (Nylon®, DuPont), polyethylene glycol terephthalate (Mylar®, DuPont), metal foils, ionomer resins (Surlyn®, DuPont), polyolefin, polyethylene, polypropylene, polyvinyl chloride (PVC), polyurethane, and ethyl vinyl acetate (EVA) co-polymer.

20. The fluid warming cassette of claim 1 in which the first sheet includes a plurality of layers and the second sheet includes a plurality of layers.

21. The fluid warming cassette of claim 20 in which the first sheet includes an inner layer and an outer layer laminated to the inner layer; and
in which the second sheet includes an inner layer and an outer layer laminated to the inner layer.

22. The fluid warming cassette of claim 21 in which the inner layers of the first and second sheets are formed from a first material having a first melting point, and the outer layers of the first and second sheets are formed from a second material having a second melting point which is higher than the first melting point.

23. The fluid warming cassette of claim 21 in which the inner layers of the first and second sheets are joined by a thermo-bond or by extrusion coating.

24. The fluid warming cassette of claim 21 in which the outer layer material is selected from the group of materials consisting of polyester, polyamide, polyethylene glycol terephthalate, metal foils, and ionomer resins.

25. The fluid warming cassette of claim 21 in which the inner layer material is selected from the group of materials consisting of polyolefin (polyethylene, polypropylene), polyvinyl chloride (PVC), polyurethane, and ethyl vinyl acetate (EVA) co-polymer.

26. The fluid warming cassette of claim 1 in which the fluid channel has a serpentine pattern.

27. A fluid warming cassette comprising:
a flexible, planar fluid container with a periphery, two edges, a proximal end, and a distal end;
a fluid channel in the fluid container, the fluid channel having two ends;
first and second rails disposed in the fluid container, inside the periphery, near the first and second edges, respectively;
at least one of the rails for keying the fluid warming cassette for insertion into a fluid warming unit
a planar stiffener near the proximal end, separate from the first and second rails, disposed in the fluid container, and extending between the rails for substantially the width of the fluid container from near the first rail to near the second rail; and
two fluid ports on the fluid container, each fluid port in fluid communication with a respective end of the fluid channel and disposed perpendicularly to the fluid container.

28. A fluid warming cassette comprising:
a flexible fluid container with two edges and two ends;
a fluid channel in the fluid container;
first and second rails disposed in the fluid container, near first and second edges of the fluid container, respectively; and
a handle portion near a proximal end of the fluid container and including a planar piece sandwiched in the fluid container between the rails for substantially the width of the fluid container.

29. The fluid warming cassette of claim 28, in which the planar piece is for stiffening the fluid container transversely between the first and second rails.

30. The fluid warming cassette of claim 28, in which at least one rail has a shape for keying the insertion of the cassette into a fluid warming unit.

31. The fluid warming cassette of claim 30, further including an inlet port, perpendicular to the fluid container and opening into the fluid channel, and an outlet port, perpendicular to the fluid container and opening into the fluid channel.

32. The fluid warming cassette of claim 31, in which the planar piece has a first section extending transversely between the rails, near the end, and a second section extending from the first section toward the fluid channel.

33. A fluid warming kit, including:
a fluid warming cassette constituted of a flexible, planar fluid container with a periphery, two edges, a proximal end, and a distal end, a fluid channel in the fluid container, rails disposed in the fluid container, inside the periphery, near the edges, a planar stiffener near the proximal end, separate from the rails, disposed in the fluid container, and extending between the rails for substantially the width of the fluid container from near the first rail to near the second rail, and inlet and outlet ports perpendicular to the fluid warming cassette and opening into the fluid channel;

an inlet line including an inlet end for receiving fluid from one or more sources, a drip chamber, and an outlet coupled to the inlet port; and an outlet line including a bubble trap with an inlet coupled to the outlet port and an outlet, an injection site coupled to the outlet of the bubble trap, and an outlet end for delivering warmed fluid.

* * * * *

UNITED STATES PATENT AND TRADEMARK OFFICE
CERTIFICATE OF CORRECTION

PATENT NO. : 7,316,666 B1  Page 1 of 1
APPLICATION NO. : 10/822580
DATED : January 8, 2008
INVENTOR(S) : Entenman et al.

It is certified that error appears in the above-identified patent and that said Letters Patent is hereby corrected as shown below:

Column 7, line 22
After "24," add "25".

Signed and Sealed this

Sixteenth Day of March, 2010

David J. Kappos
*Director of the United States Patent and Trademark Office*